United States Patent [19]

Rieber et al.

[11] Patent Number: 4,492,689
[45] Date of Patent: Jan. 8, 1985

[54] HALOGENATED 1-HYDROXYPYRAZOLES AND THEIR USE AS PESTICIDES

[75] Inventors: Norbert Rieber, Mannheim; Heinrich Böehm, Neuhofen; Heinrich Adolphi, Limburgerhof, all of Fed. Rep. of Germany

[73] Assignee: BASF Aktiengesellschaft, Fed. Rep. of Germany

[21] Appl. No.: 465,269

[22] Filed: Feb. 9, 1983

[51] Int. Cl.³ .................. A01N 57/16; C07F 9/65
[52] U.S. Cl. ................... 424/200; 548/116
[58] Field of Search .................. 548/116; 424/200

[56] References Cited

U.S. PATENT DOCUMENTS 2,754,243 7/1956 Gysin et al. .................. 424/200
2,888,462 5/1959 Cannon .................. 548/375
4,315,008 2/1982 Maurer et al. .................. 424/200

FOREIGN PATENT DOCUMENTS 12344 12/1979 European Pat. Off. .
910652 3/1954 Fed. Rep. of Germany .

OTHER PUBLICATIONS

Hansen et al., The Journal of Organic Chemistry, vol. 45, 1980, pp. 76–80.

Primary Examiner—Richard Raymond
Attorney, Agent, or Firm—Keil & Weinkauf

[57] ABSTRACT

1-Pyrazolyl-phosphoric acid esters of the formula

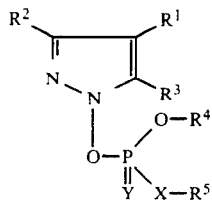

their preparation and use as crop protection agents, and their immediate precursors, i.e. halogenated 1-hydroxypyrazoles of the formula

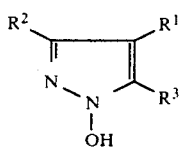

where $R^1$ to $R^5$, X and Y have the meanings given in the claims and description.

13 Claims, No Drawings

HALOGENATED 1-HYDROXYPYRAZOLES AND THEIR USE AS PESTICIDES

The present invention relates to halogenated 1-hydroxypyrazoles of the general formula (I)

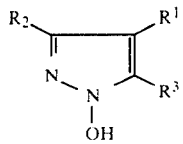

where $R^1$, $R^2$ and $R^3$ independently of one another are hydrogen, chlorine, bromine or iodine, with the proviso that $R^1$, $R^2$ and $R^3$ are not all hydrogen, which are useful intermediates, and to the novel 1-pyrazolyl-phosphoric acid esters of the general formula (II) obtainable therefrom, processes for their preparation, pest control agents containing these compounds as active ingredients, and methods of controlling pests using these active ingredients or agents.

The compounds of the formula I according to the invention can be obtained by halogenation of 1-hydroxypyrazole in a conventional manner (Houben-Weyl, Methoden der org. Chemie, Volume V/3, 725 et seq., Georg Thieme-Verlag, Stuttgart, 4th edition, 1962; Volume V/4, 38 et seq., 530 et seq., Georg Thieme-Verlag, Stuttgart, 4th edition, 1960).

In this halogenation, the corresponding mono-, di- or tri-halo-derivatives are formed, depending on the amount of halogenating agent used. Polyhalogenation can be carried out in stages, in which case derivatives containing various halogen radicals can be synthesized, or in one step.

Specifically, the halogenation is usually carried out in the presence of an inert solvent, eg. a halohydrocarbon, with or without the addition of an auxiliary base, eg. an alkali metal carbonate, by addition of the halogenating agent, eg. a halogen, an N-halo compound or a hypohalite, at from −60° to +100° C., preferably from −20° to +80° C. More or less than the molar amounts of the components can be employed, and the amount of auxiliary base is advantageously from 1 to 25 moles per mole of 1-hydroxypyrazole.

The novel compounds of the formula I are isolated in a conventional manner, for example by filtration, extraction from the reaction solution or concentration of the reaction mixture and/or fractional crystallization.

The 1-hydroxypyrazole used as the starting substance is obtained as a mixture with isoxazoles of the formula

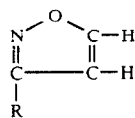

where R is hydrogen or an aliphatic, cycloaliphatic, araliphatic or aromatic radical, by heating an isoxazolineazoxy compound of the formula Ia

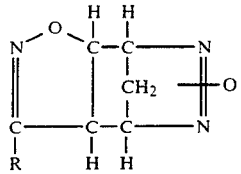

where R has the above meanings, to 140°–600° C.

If 2,3-azoxy-6-oxa-7-aza-tricyclo-[5.2.1.0^{5.9}]-deca-2,7-diene is used, the reaction can be represented by the following equation:

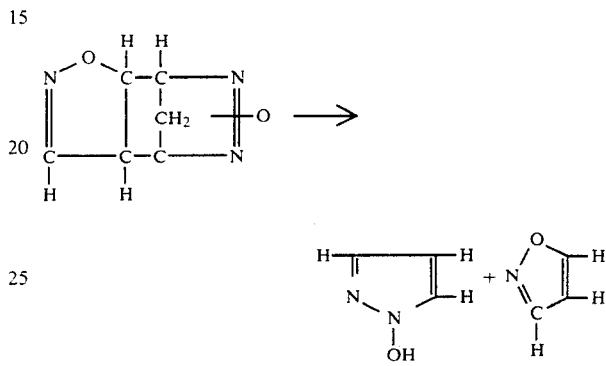

Preferred starting substances of the formula Ia are those where R is hydrogen, alkyl of 1 to 18, in particular 1 to 6, carbon atoms, cycloalkyl of 5 to 8 carbon atoms, aralkyl of 7 to 12 carbon atoms, unsubstituted phenyl or phenyl which is substituted by bromine, fluorine, chlorine, and/or alkyl and/or alkoxy of 1 to 4 carbon atoms. The above radicals may also be substituted by groups and/or atoms which are inert under the reaction conditions, eg. alkyl and alkoxy of 1 to 4 carbon atoms, and bromine, fluorine and chlorine as substituents on phenyl.

The starting substances Ia can easily be obtained by reacting a 2,3,7-triaza-6-oxa-tricyclo-[5.2.1.0^{5.9}]-deca-2,7-diene of the formula Ib

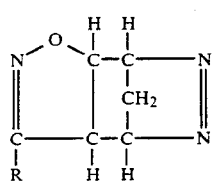

where R has the above meanings, with an organic peroxide at from −10° to +130° C., preferably from 20° to 100° C. and especially from 50° to 90° C., under atmospheric or superatmospheric pressure, continuously or batchwise, in the presence or absence of an organic solvent, eg. a halohydrocarbon or ether. The stoichiometric amount or an excess of peroxide can be used, and from 1 to 10, preferably from 1 to 1.5, moles of peroxide are preferably reacted per mole of starting substance.

The starting substances Ib can easily be obtained by reacting, in a first step, a nitrile oxide of the formula Ic $$R^1CNO \qquad\qquad\qquad (Ic)$$

where $R^1$ has the above general and preferred meanings, with an N,N'-dicarbalkoxy-2,3-diaza-bicyclo-[2.2.1]-hept-2-ene of the formula Id

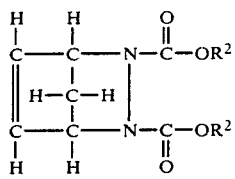

where the individual radicals $R^2$ are identical or different and each is hydrogen or an aliphatic radical, and then, in a 2nd step, in a conventional manner, hydrolyzing the resulting N,N'-dicarbalkoxy-isoxazolino compound of the formula Ie

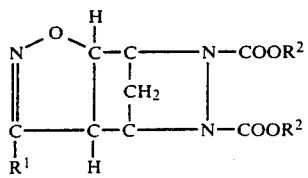

where $R^1$ has the above meanings, and decarboxylating the acid.

The starting substances Ic are easily accessible by the procedures described in Houben-Weyl, Methoden der Organischen Chemie, Volume 10/3, pages 841–853, for example by dehydrogenation of aldoximes or from hydroxamic acid derivatives or nitrolic acids. The starting substances Id are obtained, for example, by reacting cyclopentadiene with a dimethyl azodicarboxylate by one of the processes described in Ann. 443 (1925), 242–262. The oxygen in the azoxy group can be bonded to one or other of the nitrogen atoms of the azo group. Thus, the pure isomers

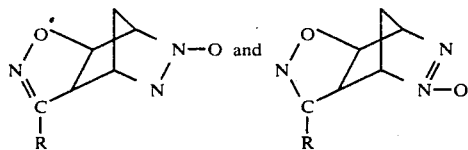

or, advantageously, the isomer mixture as obtained by the manufacturing method, can be used as the starting substances Ia.

Examples of suitable starting substances Ia are therefore 2,3-azoxy-6-oxa-7-aza-tricyclo-[5.2.1.0$^{5.9}$]-deca-2,7-diene and its homologs substituted in the 8-position by methyl, ethyl, propyl, isopropyl, butyl, isobutyl, sec.-butyl, tert.-butyl, cyclohexyl, cyclopentyl, benzyl, phenyl, 2'-chlorophenyl, 3'-chlorophenyl, 4'-chlorophenyl, 2'-methylphenyl, 3'-methylphenyl, 4'-methylphenyl, 2'-methoxyphenyl, 3'-methoxyphenyl, 4'-methoxyphenyl, 2'-ethylphenyl, 3'-ethylphenyl, 4'-ethylphenyl, 2'-ethoxyphenyl, 3'-ethoxyphenyl or 4'-ethoxyphenyl.

The reaction is carried out at from 140° to 600° C., preferably from 150° to 500° C., ie. advantageously at from 200° to 600° C., preferably from 250° to 500° C. and especially from 300° to 450° C. if R hydrogen or an aliphatic, cycloaliphatic or araliphatic radical, or at from 140° to 200° C., preferably from 150° to 190° C. and especially from 160° to 180° C. if R is an aromatic radical, under atmospheric, reduced or superatmospheric pressure, continuously or batchwise, in the presence or, for economic reasons alone, advantageously in the absence of an organic solvent which is inert under the reaction conditions.

The reaction can be carried out by heating the starting substance Ia at the reaction temperature for from one second to 21 hours and then separating off the 1-hydroxypyrazole and the isoxazole from the reaction mixture in a conventional manner, for example by fractional distillation or condensation, extraction or crystallization.

1-Hydroxypyrazole can be obtained by, for example, passing 97 parts by weight of 8-methyl-2,3-azoxy-6-oxa-7-aza-tricyclo-[5.2.1.0$^{5.9}$]-deca-2,7-diene through a tube reactor, filled with 300 parts of quartz rings, at 455° C. under 5 mbar in the course of 2 hours. The reaction mixture is subjected to fractional condensation in 2 receivers. 47 parts by weight (97% of theory) of 1-hydroxypyrazole of melting point 75° C. (from naphtha) are obtained in the first receiver, which is cooled to 5° C. The second receiver, which is cooled to −70° C., contains 46 parts by weight (95% of theory) of 3-methyl-isoxazole of boiling point 117° C.

Examples A to D which follow illustrate the preparation of compounds of type I according to the invention.

EXAMPLE A

A solution of 42 parts by weight of bromine in 300 parts by weight of methylene chloride was added to 20 parts by weight of 1-hydroxypyrazole and 50 parts by weight of $Na_2CO_3$ in 700 parts by weight of methylene chloride at 0° C., with stirring. Stirring was continued for another hour and the mixture was then filtered, the filtrate was concentrated in a rotary evaporator at from 20° to 40° C./20 mbar and the resulting residue was recrystallized from naphtha to give 39 parts by weight (91% of theory) of 1-hydroxy-4-bromopyrazole of melting point 136° C.

EXAMPLE B

A solution of 36 parts of iodine in 1,500 parts of chloroform was added to 4 parts by weight of 1-hydroxypyrazole and 10 parts by weight of $Na_2CO_3$ in 1,000 parts by weight of chloroform at the reflux temperature, with stirring. Stirring under reflux was continued for a further 24 hours, and the solid product was then filtered off with suction and suspended in 200 parts by weight of water. The suspension was acidified to pH 4 with 10 percent strength hydrochloric acid, and the solid product was filtered off with suction and dissolved in methylene chloride. The solution was dried with magnesium sulfate and filtered, and the filtrate was concentrated in a rotary evaporator at from 20° to 40° C. under 20 mbar. The residue was recrystallized from toluene to give 13.5 parts by weight (61% of theory) of 1-hydroxy-3,4,5-triiodopyrazole of melting point 153° C. (decomposition).

EXAMPLE C 9 parts by weight of iodine in 50 parts by weight of saturated aqueous potassium iodine solution were added to 3 parts by weight of 1-hydroxypyrazole and 1 part by weight of ethylenediamine, as a 60 percent strength aqueous solution, in 10 parts by weight of ethanol at 20° C., with stirring. Stirring was continued for another 2 hours, and the reaction mixture was then poured into dilute aqueous sodium thiosulfate solution. The solid product was filtered off with suction and dissolved in methylene chloride, and the solution was dried with magnesium sulfate and concentrated in a rotary evaporator at from 20° to 40° C. under 20 mbar. The residue was recrystallized from naphtha to give 6 parts by weight (80% of theory) of 1-hydroxy-4-iodopyrazole of melting point 126° C.

EXAMPLE D 81 parts by weight of bromine were added to 30 parts by weight of 1-hydroxy-4-chloropyrazole and 0.5 part by weight of iron powder in 300 parts by weight of 1,2-dichloroethane at 60° C., with stirring. Stirring was continued at 60° C. for another 2 hours, and the solid product was then filtered off with suction and recrystallized from naphtha to give 55 parts by weight (78% of theory) of 1-hydroxy-3,5-dibromo-4-chloropyrazole of melting point 160° C.

The following compounds of the formula I can be obtained in a manner similar to that in Example A, B, C or D:

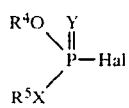

| $R^1$ | $R^2$ | $R^3$ | Melting point [°C.] |
|-------|-------|-------|---------------------|
| Cl | H | H | 122 |
| Br | Br | H | 162 |
| Br | Cl | H |  |
| Br | I | H |  |
| Cl | Br | H |  |
| Cl | I | H |  |
| Cl | Cl | H | 138 |
| I | Br | H |  |
| I | Cl | H |  |
| Cl | Cl | Cl | 172 |
| Br | Cl | Cl |  |
| Cl | I | I |  |
| Br | Br | Br | 169 |
| Br | I | I |  |
| I | Br | Br |  |
| I | Cl | Cl |  |

Reaction of the halogenated 1-hydroxypyrazoles of the formula I with phosphoric acid ester halides IIa gives 1-pyrazolylphosphoric acid esters (II), which can be used for controlling animal pests and have a particularly high specific activity.

1-Pyrazolyl-phosphoric acid esters have not yet been described in the literature. Only 4- and 5-pyrazolylphoshoric acid esters have been disclosed (German Pat. No. 910,652 and European Laid-Open Application No. 12,344).

The phosphoric acid esters of the formula II

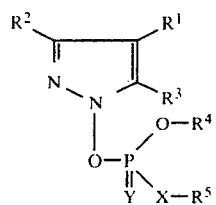

where $R^1$, $R^2$ and $R^3$ have the above meanings, $R^4$ and $R^5$ are identical or different and each is alkyl of 1 to 6 carbon atoms, and X and Y are oxygen or sulfur, can be obtained in a conventional manner by reacting a (thio)-phosphoric acid (thio)ester halide of the formula IIa

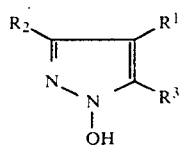

where $R^4$, $R^5$, X and Y have the above meanings and Hal is halogen, with a 1-hydroxypyrazole derivative of the formula I

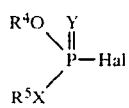

where $R^1$, $R^2$ and $R^3$ have the above meanings, in the presence of an acid acceptor, or with a salt of a 1-hydroxypyrazole derivative.

Straight-chain or branched $C_1$–$C_6$-alkyl $R^4$ or $R^5$ in formula I is methyl, ethyl, n-propyl, i-propyl, i-butyl, n-butyl, s-butyl, n-pentyl, i-pentyl, n-hexyl or i-hexyl, preferably $C_1$–$C_4$-alkyl, especially ethyl.

The reaction is preferably carried out in the presence of a suitable solvent, such as any inert solvent, eg. an aliphatic or aromatic hydrocarbon or halohydrocarbon, such as gasoline, toluene, xylene, methylene chloride, chloroform or chlorobenzene, an ether, such as diethyl ether, dibutyl ether, tetrahydrofuran or dioxane, a ketone, such as acetone, methyl ethyl ketone, methyl isopropyl ketone or methyl isobutyl ketone, or a nitrile, such as acetonitrile or propionitrile.

The conventional acid acceptors can be used, eg. alkali metal carbonates or alcoholates or aliphatic, aromatic or heterocyclic amines.

The reaction can be carried out at from 0° to 100° C., preferably from 10° to 60° C.

Equimolar amounts of the starting substances are usually employed, but it is also possible to use more or less than these amounts.

The reaction mixture is worked up in a conventional manner, for example by filtration and distillation of the solvent, if necessary after extraction of the organic phase with water or aqueous $NaHCO_3$ solution or sodium carbonate solution. If a water-soluble solvent has been used, a water-immiscible solvent is added before the extraction.

The (thio)phosphoric acid (thio)ester halides are known, and can be prepared in a conventional manner (German Laid-Open Application DOS No. 2,642,982; J. Org. Chem. 30, 3217 (1965)).

Preparation of O-pyrazol-1-yl O,O-diethyl thiophosphate.

112 part of diethyl thiophosphate chloride were added to 55 parts of 1-hydroxypyrazole and 50 parts of sodium carbonate in 600 parts of acetonitrile at 25° C., with stirring. Stirring was continued for another 12 hours. The solid product was filtered off with suction and washed with two portions of 50 parts of acetonitrile. The filtrate was concentrated in a rotary evaporator at from 20° to 40°C. under 20 mbar. The residue as dissolved in 300 parts by weight of methylene chloride, the organic phase was extracted with three portions of 50 parts by weight of saturated aqueous NaHCO$_3$ solution, the methylene chloride solution was dried with magnesium sulfate and the solvent was stripped off in a rotary evaporator at from 20° to 40° C. under 20 mbar to give 127.5 parts by weight (91% of theory) of O-pyrazol-1-yl O,O-diethyl thiophosphate.

H$^1$—NMR (δ in ppm): 1.3 (t, 6H); 4.3 (m, 4H); 6.2 (m, 1H); 7.25 (m, 1H); 7.4 (m, 1H).

The substituentes shown in the Table in each case relate to a compound of the formula II

| No. | R$^1$ | R$^2$ | R$^3$ | Y | X | R$^4$ | R$^5$ | H$^1$—NMR (δ in ppm) |
|---|---|---|---|---|---|---|---|---|
| 1 | Br | H | H | S | S | C$_2$H$_5$ | i-C$_4$H$_9$ | 1.0(d, 6H), 1.4(t, 3H), 1.8(m, 1H), 2.8(m, 2H), 4.3(m, 2H), 7.3(s, 1H), 7.5(s, 1H) |
| 2 | H | " | " | " | " | " | " | 1.0(d, 6H), 1.4(t, 3H), 1.9(m, 1H), 2.8(m, 2H), 4.3(m, 2H), 6.2(m, 1H), 7.2(m, 1H), 7.4(m, 1H) |
| 3 | Cl | " | " | " | " | " | " | 1.0(d, 6H), 1.35(t, 3H), 1.9(m, 1H), 2.8(m, 2H), 4.3(m, 2H), 7.2(s, 1H), 7.4(s, 1H) |
| 4 | Br | Br | " | " | " | " | n-C$_3$H$_7$ | 1.0(t, 3H), 1.7(m, 2H), 3.0(m, 2H), 4.35(m, 2H), 7.45(s, 1H) |
| 5 | " | " | Br | " | O | CH$_3$ | CH$_3$ | 3.8(s, 3H), 4.1(s, 3H) |
| 6 | " | H | H | " | " | C$_2$H$_5$ | C$_2$H$_5$ | 1.4(t, 6H), 4.3(m, 4H), 7.2(s, 1H), 7.4(s, 1H) |
| 7 | " | Br | " | " | " | " | " | 1.4(t, 6H), 4.3(m, 4H), 7.4(s, 1H) |
| 8 | " | " | " | " | " | CH$_3$ | CH$_3$ | 3.8(s, 3H), 4.1(s, 3H), 7.4(s, 1H) |
| 9 | " | " | Br | " | " | C$_2$H$_5$ | C$_2$H$_5$ | 1.3(m, 6H), 4.3(m, 4H) |
| 10 | " | " | " | " | S | " | n-C$_3$H$_7$ | 0.7-1.7(m, 8H), 2.7(m, 2H), 4.35(m, 2H) |
| 11 | Cl | E | H | " | O | CH$_3$ | CH$_3$ | 3.8(s, 3H), 4.0(s, 3H), 7.25(s, 1H), 7.4(s, 1H) |
| 12 | Br | " | " | " | " | " | " | 3.8(s, 3H), 4.0(s, 3H), 7.2(s, 1H), 7.4(s, 1H) |
| 13 | " | " | " | " | S | C$_2$H$_5$ | n-C$_3$H$_7$ | 1.0(t, 3H), 1.4(t, 3H), 1.7(m, 2H), 3.0(m, 2H), 4.3(m, 2H), 7.2(s, 1H), 7.45(s, 1H) |
| 14 | Cl | " | " | " | O | " | C$_2$H$_5$ | 1.4(t, 6H), 4.35(m, 4H), 7.25(s, 1H), 7.45(s, 1H) |
| 15 | H | H | " | O | " | " | " | 1.35(t, 6H), 4.3(m, 4H), 6.2(m, 1H), 7.2(m, 1H), 7.4(m, 1H) |
| 16 | " | " | " | S | " | " | " | 1.4(t, 6H), 4.3(m, 4H), 6.2(m, 1H), 7.25(m, 1H), 7.4(m, 1H) |
| 17 | " | " | " | " | " | CH$_3$ | CH$_3$ | 3.8(s, 3H), 4.0(s, 3H), 6.2(m, 1H), 7.25(m, 1H), 7.4(m, 1H) |
| 18 | " | " | " | " | S | C$_2$H$_5$ | n-C$_3$H$_7$ | 1.0(t, 3H), 1.4(t, 3H), 1.75(m, 2H), 3.0(m, 2H), 4.35(m, 2H), 6.2(m, 1H), 7.25(m, 1H), 7.4(m, 1H) |
| 19 | Cl | " | " | " | " | " | " | 1.0(t, 3H), 1.4(t, 3H), 1.7(m, 2H), 3.0(m, 2H), 4.35(m, 2H), 7.2(s, 1H), 7.5(s, 1H) |
| 20 | I | " | " | " | O | " | C$_2$H$_5$ | 1.4(t, 6H), 4.3(m, 4H), 7.3(s, 1H), 7.5(s, 1H) |
| 21 | " | " | " | " | " | CH$_3$ | CH$_3$ | 3.8(s, 3H), 4.05(s, 3H), 7.35(s, 1H), 7.45(s, 1H) |
| 22 | Cl | Br | Br | " | " | C$_2$H$_5$ | C$_2$H$_5$ | 1.4(m, 6H), 4.4(m, 4H) |
| 23 | " | " | " | " | " | CH$_3$— | CH$_3$— | 3.85(bs, 3H), 4.15(bs, 3H) |
| 24 | Br | H | H | " | S | C$_2$H$_5$ | s-C$_4$H$_9$ | 0.8-2.0(m, 11H), 3.6(m, 1H), 4.3(m, 2H), 7.3(s, 1H), 7.5(s, 1H) |
| 25 | H | " | " | " | " | " | " | 0.8-2.1(m, 11H), 3.6(m, 1H), 4.4(m, 2H), 6.3(m, 1H), 7.3(s, 1H), 7.5(s, 1H) |
| 26 | Cl | Cl | Cl | " | O | " | C$_2$H$_5$ | 1.35(m, 6H), 4.35(m, 4H) |
| 27 | I | I | I | " | " | " | " | 1.3(m, 6H), 4.3(m, 4H) |
| 28 | H | H | H | O | " | " | n-C$_6$H$_{13}$ | |
| 29 | Cl | " | " | S | S | " | i-C$_5$H$_{11}$ | |
| 30 | I | " | " | " | O | " | n-C$_5$H$_{11}$ | |
| 31 | H | " | " | O | " | n-C$_6$H$_{13}$ | C$_2$H$_5$ | |
| 32 | Cl | Cl | " | S | " | C$_2$H$_5$ | i-C$_6$H$_{13}$ | |
| 33 | Br | H | " | " | " | " | C$_2$H$_5$ | |
| 34 | H | " | " | O | S | " | i-C$_4$H$_9$ | |

German Laid-Open Application DE-OS No. 30 39 080 and European Publication No. 0050219, which relate to structurally similar active ingredients, give the insects and Arachnida which can be combated, and details on formulation and suitable mixture components.

As the following test results show, these 1-pyrazolphosphoric acid esters are suitable for combating pests from the classes of insects and Arachnida. The comparative agent was the prior art compound O,O dimethyl-S-(1,2-bis-carbethoxy-ethyl)-phosphorodithioate (German Pat. No. 847,897). The active ingredients are numbered as in the Table.

EXAMPLE 1

Contact action and effect of ingested food an caterpillars of the diamondback moth (*Plutella maculipennis*)

Leaves of young cabbage plants were dipped for 3 seconds in aqueous emulsions of the active ingredients, and, after briefly having allowed excess liquid to drip off, were placed on a moist filter paper in a Petri dish. 10 caterpillars of the 4th stage were then placed on the leaves. The action was assessed after 48 hours.

In this test, active ingredients nos. 1, 2, 3, 6, 14 and 16 had a better action than the comparative agent.

EXAMPLE 2

Contact action on oriental cockroaches (*Blatta orientalis*)

The bottom of 1 liter preserving jars was lined with acetonic solutions of the active ingredients. After the solvent had evaporated, 5 adult cockroaches were introduced into each jar. The kill rate was determined after 48 hours.

In this test, active ingredients nos. 2, 6, 7, 11, 12, 14, 15, 16 and 18 had a good action.

EXAMPLE 3

Contact action on ticks (*Ornithodorus moubata*)

The experiment was carried out on young ticks which had sucked blood only once. Paper bags, each containing 5 animals, were dipped for 5 seconds in the aqueous active ingredient formulation. The bags were then suspended. The temperature was kept at 25° to 26° C. The kill rate was determined after 48 hours.

In this test, active ingredients nos. 2, 6, 7, 14, 15, 16, 17, and 18 had a better action than the comparative agent.

EXAMPLE 4

Contact action on cotton stainers (*Dysdercus intermedius*)

Petri dishes 10 cm in diameter were lined with 1 ml of acetonic solutions of the active ingredients. After the solvent had evaporated, 20 larvae of the penultimate stage were placed in the dishes, and the effect was registered after 24 hours.

In this test, active ingredients nos. 1, 2, 3, 6, 7, 8, 9, 11, 12, 13, 14, 15, 16, 18 and 20 had a good action.

EXAMPLE 5

Systemic action on caterpillars (*Prodenia litura*)

200 ml of quartz sand was filled into 250 ml plastic beakers, which were then placed in 8-vessel pallets. 5 Indian corn grains were introduced into each beaker (about 1 cm beneath the surface). Each beaker was then moistened with 50 ml of water and covered with a fitting transparent plastic hood. After 8 days, the hoods were removed and treatment was effected after 10 days. Each beaker was watered with 40 ml of the aqueous active ingredient formulations, and, after a further day, 50 ml of dry quartz sand was added as a cover to each beaker. The purpose of this sand cover was to prevent the test animals from coming into contact with the treated surface.

Plastic cylinders 7 cm in diameter were placed on each beaker, 5 caterpillars in the 3rd larval stage were introduced, and the cylinders were capped with a wire gauze cover. Eating and mortality in the vessels were assessed after 4 days.

In this test, active ingredients nos. 2, 3, 6, 9, 13, 14 and 16 had a better action than the comparative agent.

EXAMPLE 6

Contact action of bean aphids (*Aphis fabae*), spray experiment

Potton bean plants (*Vicia faba*) with extensive bean aphid colonies were sprayed to runoff in a spray booth with aqueous formulations of the active ingredients. Assessment took place after 48 hours.

In this test, active ingredients nos. 1, 2, 3, 6, 7, 12, 13, 14, 15, 16, 17, 18 and 20 had a good action.

EXAMPLE 7

Continuous contact action on houseflies (*Musca domestica*)

Both covers and bottoms of Petri dishes 10 cm in diameter were lined with a total per dish of 2 ml of acetonic solutions of the active ingredients. After the solvent had evaporated (about 30 mins.), 20 4-day old flies were introduced into each dish.

The kill rate was determined after 4 hours.

In this test, active ingredients nos. 1, 2, 6, 7, 13, 14, 15, 16, 18 and 20 achieved a higher kill rate than the comparative agent.

EXAMPLE 8

Contact action on houseflies (*Musca domestica*)

1 μl of the active ingredient dissolved in acetone was administered with a microsyringe to the ventral abdomen of 4-day old imagoes under slight $CO_2$ narcosis. 20 animals treated in the same way were placed in a plastic bag having a volume of approximately 500 ml.

After 4 hours, animals in supine position were counted, and the $LD_{50}$ was worked out by means of a graph.

The $LD_{50}$ of active ingredients nos. 6, 7, 15 and 16 is lower than that of the comparative agent.

We claim:

1. A 1-pyrazolyl-phosphoric acid ester of the formula

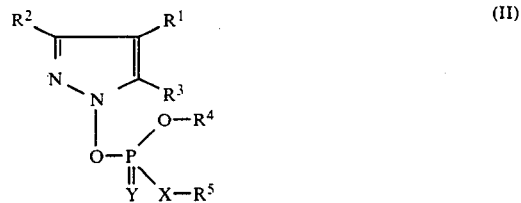

where $R^1$, $R^2$ and $R^3$ independently of one another are hydrogen, chlorine, bromine or iodine, with the proviso that $R^1$, $R^2$ and $R^3$ are not all hydrogen, $R^4$ and $R^5$ are identical or different and each is alkyl of 1 to 6 carbon atoms, and X and Y are oxygen or sulfur.

2. A 1-pyrazolyl-phosphoric acid ester of the formula II as defined in claim 1, where $R^1$ is hydrogen, chlorine or bromine, $R^2$ is hydrogen, $R^3$ is hydrogen, $R^4$ is ethyl, $R^5$ is ethyl, X is oxygen and Y is oxygen or sulfur, with the proviso that $R^1$, $R^2$ and $R^3$ are not all hydrogen.

3. A compound of the formula II as defined in claim 1, wherein $R^1$ is chloro and $R^2$ and $R^3$ are hydrogen.

4. A compound of the formula II as defined in claim 1, wherein $R^1$ is bromo and $R^2$ and $R^3$ are hydrogen.

5. A compound of the formula II as defined in claim 1, wherein $R^1$ and $R^2$ are chloro and $R^3$ is hydrogen.

6. A compound of the formula II as defined in claim 1, wherein $R^1$, $R^2$ and $R^3$ are each chloro.

7. A compound of the formula II as defined in claim 1, wherein $R^1$ and $R^2$ are bromo and $R^3$ is hydrogen.

8. A compound of the formula II as defined in claim 1, wherein $R^1$, $R^2$ and $R^3$ are each bromo.

9. A compound of the formula II as defined in claim 1, wherein $R^1$ is chloro and $R^2$ and $R^3$ are bromo.

10. A compound of the formula II as defined in claim 1, wherein $R^1$ is iodo and $R^2$ and $R^3$ are hydrogen.

11. A compound of the formula II as defined in claim 1, wherein $R^1$, $R^2$ and $R^3$ are each iodo.

12. A pesticide containing inert additives and an effective amount of a 1-pyrazolyl-phosphoric acid ester of the formula II as defined in claim 1.

13. A process for combatting pests, wherein the pests and/or their habitat are contacted with an effective amount of a 1-pyrazolyl-phosphoric acid ester of the formula II as defined in claim 1.

* * * * *